US008840919B2

(12) United States Patent
Davidson

(10) Patent No.: US 8,840,919 B2
(45) Date of Patent: Sep. 23, 2014

(54) METHOD AND APPARATUS FOR MINIMIZING HEAT, MOISTURE, AND SHEAR DAMAGE TO MEDICANTS AND OTHER COMPOSITIONS DURING INCORPORATION OF SAME WITH EDIBLE FILMS

(75) Inventor: Robert S. Davidson, Woodland Hills, CA (US)

(73) Assignee: CURE Pharmaceutical Corporation, Oxnard, CA (US)

( * ) Notice: Subject to any disclaimer, the term of this patent is extended or adjusted under 35 U.S.C. 154(b) by 1181 days.

(21) Appl. No.: 11/836,758

(22) Filed: Aug. 9, 2007

(65) Prior Publication Data

US 2007/0275040 A1 Nov. 29, 2007

Related U.S. Application Data

(62) Division of application No. 10/402,273, filed on Mar. 28, 2003, now abandoned.

(51) Int. Cl.
 *A61K 9/70* (2006.01)
 *B05D 3/00* (2006.01)
 *A61K 9/00* (2006.01)

(52) U.S. Cl.
 CPC ............. *A61K 9/0056* (2013.01); *A61K 9/7007* (2013.01); *A61K 9/0051* (2013.01)
 USPC .......................................... 424/443; 427/231

(58) Field of Classification Search
 USPC ........................... 424/449, 486, 443; 427/2.31
 See application file for complete search history.

(56) References Cited

U.S. PATENT DOCUMENTS

| | | | |
|---|---|---|---|
| 3,931,146 A | 1/1976 | Kato et al. | |
| 4,072,551 A | 2/1978 | Dabal et al. | |
| 4,083,741 A | 4/1978 | Goldberg | |
| 4,517,173 A | 5/1985 | Kizawa et al. | |
| 4,876,092 A | 10/1989 | Mizobuchi et al. | |
| 5,047,244 A | 9/1991 | Sanvordeker et al. | |
| 5,055,461 A | 10/1991 | Kelleher et al. | |
| 5,166,233 A | 11/1992 | Kuroya et al. | |
| 5,196,202 A | 3/1993 | Konishi | |
| 5,411,945 A | 5/1995 | Ozaki et al. | |
| 5,629,003 A | 5/1997 | Horstmann et al. | |
| 5,700,478 A | 12/1997 | Biegajski et al. | |
| 5,948,430 A | 9/1999 | Zerbe et al. | |
| 6,010,716 A | 1/2000 | Saunal et al. | |
| 6,177,096 B1 | 1/2001 | Zerbe et al. | |
| 6,284,264 B1 | 9/2001 | Zerbe et al. | |
| 6,419,903 B1 | 7/2002 | Xu et al. | |
| 6,449,925 B1 | 9/2002 | Otsu et al. | |
| 6,596,298 B2 | 7/2003 | Leung et al. | |
| 6,660,292 B2 | 12/2003 | Zerbe et al. | |
| 6,783,768 B1 | 8/2004 | Brown et al. | |
| 7,025,983 B2 | 4/2006 | Leung et al. | |
| 7,067,116 B1 | 6/2006 | Bess et al. | |
| 7,132,113 B2 | 11/2006 | Zerbe et al. | |
| 7,261,939 B2 * | 8/2007 | Hallett et al. | 428/403 |
| 2001/0006677 A1 | 7/2001 | McGinity et al. | |
| 2001/0022964 A1 | 9/2001 | Leung et al. | |
| 2001/0055613 A1 * | 12/2001 | Burnside et al. | 424/468 |
| 2002/0019447 A1 | 2/2002 | Renn et al. | |
| 2002/0131990 A1 | 9/2002 | Barkalow et al. | |
| 2003/0008008 A1 | 1/2003 | Leung et al. | |
| 2003/0064097 A1 * | 4/2003 | Patel et al. | 424/465 |
| 2003/0068373 A1 * | 4/2003 | Luber et al. | 424/468 |
| 2003/0206942 A1 | 11/2003 | Kulkarni et al. | |
| 2003/0211136 A1 | 11/2003 | Kulkarni et al. | |
| 2004/0096569 A1 | 5/2004 | Barkalow et al. | |
| 2004/0131662 A1 | 7/2004 | Davidson | |
| 2004/0136922 A1 | 7/2004 | Leung et al. | |
| 2004/0136923 A1 | 7/2004 | Davidson | |
| 2004/0191302 A1 | 9/2004 | Davidson | |
| 2004/0247649 A1 | 12/2004 | Pearce et al. | |
| 2005/0031675 A1 | 2/2005 | Leung et al. | |
| 2005/0089548 A1 | 4/2005 | Virgalitto et al. | |
| 2006/0039953 A1 | 2/2006 | Leung et al. | |
| 2006/0147493 A1 | 7/2006 | Yang et al. | |
| 2006/0205629 A1 | 9/2006 | MacQuarrie | |
| 2006/0210610 A1 | 9/2006 | Davidson et al. | |
| 2007/0087036 A1 | 4/2007 | Durschlag et al. | |
| 2007/0122455 A1 | 5/2007 | Myers et al. | |

FOREIGN PATENT DOCUMENTS

| | | |
|---|---|---|
| CA | 2 520 986 A | 4/2000 |
| EP | 0163924 B1 | 12/1985 |
| EP | 0262422 A | 4/1988 |

(Continued)

OTHER PUBLICATIONS

Blachford, Metallic Stearates (http://blachford.ca/stearates-metallic.php), Jun. 4, 2011.*
Database WPI, Section Ch, Week 200375, Derwent Publications Ltd., London, GB; XP-002322049 & KR 2003 054 221 A (Aekyung Ind Co Ltd) Jul. 2, 2003 (Abstract).
Database CA Online No. XP-002346984, Chemical Abstracts Service, Columbus, Ohio, Ueshima, Yasuhide et al., "Saccharides for the Treatment of Respiratory Tract Diseases," retrieved from STN, Database Accession No. 132:146641 (Abstract), and JP2000044488A2 (Teijin Ltd., Japan), Feb. 15, 2000, 2 pages.
Patent Abstracts of Japan, vol. 015, No. 398 (C-0874), Oct. 9, 1991, and JP 03164139 A (Eitarou Souhonpo:KK), Jul. 16, 1991 (Abstract).
Supplementary European Search Report for European Patent Application No. EP03786775 dated Oct. 15, 2007 (5 pages).

(Continued)

*Primary Examiner* — Blessing M Fubara
(74) *Attorney, Agent, or Firm* — Schwegman Lundberg & Woessner, P.A.

(57) ABSTRACT

A medicant composition is provided. The composition includes a film layer and a powder matrix layer. The powder matrix layer includes a medicant. The powder matrix layer is applied to the film layer by admixing particulate to form a powder matrix and by then applying the powder matrix to the film layer by any desired method. The composition of the powder matrix is varied to alter the dissolution rate of the medicant, the adhesion of the medicant composition, and other physical properties of the powder matrix. The powder matrix layer can be cured.

10 Claims, No Drawings

(56) References Cited

FOREIGN PATENT DOCUMENTS

| | | | |
|---|---|---|---|
| FR | 2071223 A | 9/1971 | |
| WO | 94/14331 A | 7/1994 | |
| WO | WO 95/34286 A | 12/1995 | |
| WO | 97/05786 A | 2/1997 | |
| WO | 98/20861 A1 | 5/1998 | |
| WO | WO 98/20861 | * | 5/1998 |
| WO | WO 98/20863 A | 5/1998 | |
| WO | WO 00/18365 A | 4/2000 | |
| WO | WO 00/59423 | * | 10/2000 |
| WO | WO 01/35934 | 5/2001 | |
| WO | WO 01/70194 A | 9/2001 | |
| WO | 02/02085 A | 1/2002 | |
| WO | WO 02/02126 | 1/2002 | |
| WO | WO 03/015748 A | 2/2003 | |
| WO | 2004/087089 A | 10/2004 | |

OTHER PUBLICATIONS

European Patent Office, Supplemental Search Report for European Patent Application No. 04781769.7, dated Jun. 20, 2008.

U.S. Patent and Trademark Office; International Search Report and Written Opinion for International Application No. PCT/US08/80362, mailed Dec. 22, 2008.

* cited by examiner

METHOD AND APPARATUS FOR MINIMIZING HEAT, MOISTURE, AND SHEAR DAMAGE TO MEDICANTS AND OTHER COMPOSITIONS DURING INCORPORATION OF SAME WITH EDIBLE FILMS

CROSS-REFERENCE TO RELATED APPLICATIONS

The present application is a divisional of U.S. patent application Ser. No. 10/402,273, filed on Mar. 28, 2003 now abandoned, which is incorporated by reference herein in its entirety.

TECHNICAL FIELD

This invention pertains to edible compositions.

More particularly, the invention pertains to a film in which a medicant is applied as a powder.

In another respect, the invention pertains to a method for making a film that facilitates the incorporation with the film of a gel.

In a further respect, the invention pertains to a method for making a film including a medicant that minimizes the exposure of the medicant in the film to moisture, heat, and shear during the manufacturing process.

In still another respect, the invention pertains to a method for making a film that facilitates stabilizing a medicant in the film.

In yet another respect, the invention pertains to a method for applying a medicant to living cells in the body of an individual.

In yet still another respect, the invention pertains to a method for curing a film.

BACKGROUND

A wide variety of edible compositions exist in nature, are grown, or are manufactured. One particular kind of manufactured edible compositions comprises lozenges, films, and other compositions that are intended to be placed in and to dissolve or otherwise disassociate in the mouth.

U.S. Pat. No. 4,517,173 to Kizawa et al. (1985) discloses a film that adheres to mucous membrane. The film includes at least three layers. The layers are a pharmaceutical layer, a poor water-soluble layer, and an intermediate layer.

The pharmaceutical layer is a material selected from the group consisting of predonisolone and allantoin together with water-soluble cellulose derivatives. The cellulose derivatives are selected from the group consisting of hydroxypropyl cellulose, methyl cellulose, hydroxy propyl methyl cellulose and mixtures thereof.

The predonisolone, allantoin, and/or celluose derivatives form a thin film base. The poor water-soluble layer consists of water-soluble cellulose derivative together with water-soluble components. The water-soluble components are selected from the group consisting of shellac, higher fatty acids, and mixtures thereof. The intermediate layer consists of water-soluble cellulose derivatives not containing a pharmaceutical agent and not containing poor water soluble components.

Another embodiment of the film described in U.S. Pat. No. 4,517,173 includes one layer of pharmaceutical agents and water-soluble high polymer material. The other layer of the film consist of poor water-soluble agents. A first solvent solution for forming the pharmaceutical agent and water-soluble high polymer material first layer is prepared. A second solvent solution for forming the poor water-soluble agents second layer is prepared separately. The first solution is coated on a base plate having a favorable releasing nature. The solvent is removed from the solution to produce a first film layer on the base plate. The second solution is then coated on the first layer. The solvent is removed from the second solution. The solvent is removed from the second solution to form the second film layer.

By way of example, in U.S. Pat. No. 4,517,173 a solution for the film base agent for preparing the pharmaceutical layer is prepared by dissolving hydropropyl cellulose and macrogol-400 (polyethylene glycol) in ethyl alcohol and distilled water. The distilled water contains dissolved predonisolone. A solution for preparing the poor water-soluble layer is prepared by dissolving hydroxypropyl cellulose, magrogol, and shellac in ethyl alcohol. The solution for the first base agent for the intermediate layer is prepared by dissolving hydroxypropyl cellulose and magrogol in ethyl alcohol.

U.S. Pat. No. 5,948,430 to Zerbe et al. (1999) discloses a monolayer film formed from a mucoadhesive composition. The mucoadhesive composition comprises at least one water-soluble polymer, at least one member selected from the group consisting of a polyalcohol, a surfactant and a plasticizer; at least one cosmetic or pharmaceutically active ingredient; and a flavoring agent. The film rapidly softens and completely disintegrates in the oral environment and has a dry film thickness suitable for application in the mouth without causing adverse feeling in the mouth. During preparation of the film, the polyalcohol, surfactants, plasticizers, and possible other ingredients except the water-soluble or water-dispersible polymer(s) are dissolved in a sufficient amount of compatible solvent. The solvent can, for example, include water and/or alcohol. Once a clear solution is formed, the water-dispersible polymer or mixture of water dispersible polymers is slowly added with stirring, and heated if necessary, until a clear and homogeneous solution is formed. Active ingredients and flavors are added. The resulting solution is coated onto a suitable carrier material and dried to produce a film. The carrier material has a surface tension that allows the polymer solution to spread evenly across the intended coating width without soaking in to form a bond between the two. The carrier material can, for example, comprise non-siloconized polyethylene terephthalate film, on-siliconized kraft paper, polyethylene-impregnated kraft paper, or non-siliconized polyethylene film. The thickness of the film can vary between 5 and 200 um. Drying of the film is done in a high-temperature air-bath using a drying oven, drying tunnel, vacuum drier, or any other suitable drying equipment that does not adversely affect the active ingredient(s) or flavor of the film. A film thickness greater than 70 um is avoided so that an adverse feeling is not produced in the mouth.

U.S. Pat. No. 5,166,233 to Kuroya et al. (1992) describes a film that is applicable to the oral mucosa. The film comprises a homogeneous mixture. The homogenous mixture comprises a vinyl acetate homopolymer, an acrylic acid polymer, and a cellulose derivative capable of being dissolved in or swollen with water and a lower alcohol. The film also contains a salt or base to neutralize the acrylic acid polymer. The salt or base is present in an amount of from 0.03 to 0.2 equivalent to the acrylic acid polymer. The acrylic acid polymer and cellulose derivative are present at a weight ratio of from 1:9 to 9:1. The lower alcohol is methanol or ethanol. By the way of example, one procedure for preparing a film comprises mixing a vinyl acetate homopolymer, a carboxyvinyl polymer, and a hydroxypropyl cellulose to a 1:9 water/methanol solvent mixture to produce a film-forming composition.

The film-forming composition is applied to a silicone-release paper, dried, and stripped off to obtain a 30·mu·m thick adhesive film.

U.S. Pat. No. 5,047,244 to Sanvordeker, et al. (1991) describes a mucoadhesive carrier. The carrier allows controlled release of a therapeutic agent via mucosal tissue. The carrier is claimed as a "therapeutic dosage". For example, in one claim the "therapeutic dosage" comprises an anhydrous but hydratable monolithic polymer matrix containing amorphous fumed silica and a therapeutic agent. The polymer matrix defines a mucoadhesive face. A water-insoluble barrier layer is secured to the polymer matrix. The barrier layer defines a non-adhesive face. The therapeutic agent is dehydroepiandrosterone. The polymer is polyethylene glycol. The polyethylene glycol has a number average molecular weight of about 4,000. The weight ratio of dehydroepiandrosterone to polyethylene glycol is about 1:4. By way of example, the polymer matrix and barrier film are prepared separately.

The polymer matrix is prepared by dissolving the therapeutic agent in polyethylene glycol. The polyethylene glycol is melted at 160 degrees F. The powder therapeutic agent is slowly added to the molten polyethylene glycol and the glycol is stirred until the therapeutic agent is completely dissolved. The resulting composition is poured onto flat aluminum foil and allowed to solidify to form a mucosal composition. The mucosal composition is finely ground to a powder of about 60 to 80 mesh and blended with other matrix forming hydrophilic and hydrophobic excipients. Such excipients can comprise glyceryl behenate, polyvinyl alcohol, dicalcium phosphate dihydrate, hydroxypropyl cellulose and silica. Additional polyethylene glycol can be added. A granulation process utilizing an organic solvent or water can be used to prepare, dry, and obtain granules having a size in the range of 40 to 200 mesh.

The barrier film is prepared using constituents from the polymer matrix, except the barrier film does not include a therapeutic agent.

The components of the polymer matrix and barrier film are compressed together to obtain a bi-laminate mucoadhesive carrier.

U.S. Pat. No. 4,876,092 to Mizobuchi, et al. describes a sheet-shaped adhesive pharmaceutical preparation. The preparation can adhere to the oral cavity. The preparation comprises an adhesive layer and a carrier layer. The adhesive layer includes a carboxyvinyl polymer, a water-soluble methacrylic copolymer, a polyhydric alcohol, and a pharmaceutically active agent. The carrier layer is water-impermeable and water-insoluble. The carrier layer includes a pharmaceutically acceptable water-insoluble, film-forming high molecular weight compound and includes a plasticizer. The ingredients of the adhesive layer are substantially released from one side of the sheet-shaped pharmaceutical preparation. The ingredients are absorbed through the mucous membrane or teethridge to which the preparation is adhered in the oral cavity. By way of example, the adhesive layer is prepared by producing an adhesive layer mixture. The adhesive layer mixture is prepared by mixing the components for the adhesive layer in an appropriate solvent like ethyl alcohol. The resulting mixture is spread onto a release paper in a desired thickness in a conventional manner and is dried to produce a sheet-like adhesive layer. The components for the carrier layer are dissolved in an appropriate solvent to produce a carrier layer mixture. The resulting carrier layer mixture is spread onto the sheet-like adhesive layer and dried.

U.S. Patent Application US 2002/0131990 to Barkalow et al. (2002) discloses a pullulan free edible film composition. The film comprises an effective amount of at least one film forming agent; an effective amount of at least one bulk filler agent; and, an effective amount of at least one plasticizing agent. By way of example, the film is produced by adding LustreClear (a composition by FMC Corporation for use as a clear coating for pharmaceutical tablets) to water to produce a coating mixture. LustreClear contains microcrystalline cellulose, carrageenan, polyethylene glycol, hydroxyethyl cellulose and maltodextrin. The coating mixture is heated to 50 degrees C. and other ingredients are added. While the mixture is warm, the mixture is poured onto a glass plate and drawn down to form a thin film with a 0.08 inch blade. The resulting film composition is dried at 50 degrees C. for about fifteen minutes.

U.S. Patent Application US 2001/0022964 to Leung et al. (2001) discloses a consumable film. The film is adapted to adhere to and dissolve in a mouth of a consumer. The film comprises at least one water soluble polymer and an antimicrobial effective amount of at least one essential oil selected from the group consisting of thymol, methyl salicylate, eucalyptol and menthol. By way of example, a film is prepared as follows. Xanthan gum, locust bean gum, carrageenan and pullulan are mixed and hydrated in hot purified water to form a gel. The gel is stored in a refrigerator overnight at a temperature of approximately four degrees C. to form preparation A. Coloring agents, copper gluconate, and sweetener are added to and dissolved in purified water to form preparation B. Preparation B is mixed with preparation A to form preparation C. Flavoring agents and oils (including cooling agent, thymol, methyl salicylate, eucalyptol and menthol) are mixed to form preparation D. Polysorbate 80 and Atmos 300 are added to preparation D and mixed to form preparation E. Preparation E is added to preparation C and mixed to form preparation F. Preparation F is poured on a mold and cast to form a film of desired thickness at room temperature. The film is dried under warm air.

The prior art edible films and production processes each have desirable aspects. They also have disadvantages. One disadvantage is that the prior art processes may expose medicants or actives or other compositions to water or another liquid during production of the edible films. Many medicants or other compositions are unstable in the presence of water or other liquids. A second disadvantage of prior art processes is that the production process may subject a medicant or other composition to shear. Shear can damage the medicant. Shear occurs when a mixing blade or other member forces a medicant particle intermediate the blade and another solid member, generating friction and heat. A third disadvantage of prior art processes is that they may require the application of heat at temperatures or over extended periods of time that can degrade or undesirably alter the stability or properties of a medicant or other composition. A fourth potential disadvantage of prior art processes is that they may not permit, with minimal effort, the dissolution rate of a medicant or other composition to be varied. A fifth potential disadvantage of prior art processes is that they may make use of a hydrophilic component at higher concentrations impractical because during production the hydrophilic component rapidly absorbs water and become difficult to process. A sixth potential disadvantage of prior art processes is that the edible films produced are primarily suitable only for use in the oral cavity and not for use on living cells. A seventh potential disadvantage of prior art processes is that heat alone can not, practically speaking, be used to form a smooth coating on an edible film. An eighth potential disadvantage of prior art processes is that they require the use of a solvent to produce a layer including a medicant or other desired composition. A ninth potential disadvantage of the prior art processes is that they require the compatibility of a medicant with other components in a solvent solution to be taken into account.

Accordingly, it would be highly desirable to provide an improved edible film and process for making the same that would minimize the risk that a medicant or other composition is degraded or otherwise damaged by heat, shear, or moisture; that would permit the dissolution rate of a medicant to be readily varied, that would permit the ready use of a hydrophilic composition, that could be utilized on live cells, that would facilitate the use of heat to form a coating on an edible film, and that would not require the use of a solvent to mix compositions to form a medicant-containing layer.

I have discovered an improved film and method for making the same. The film can be used on living cells. Formation of the medicant-containing layer in the film does not require a solvent and minimizes the likelihood of damage from heat and shear. The rate of dissolution or delivery of the medicant by the film can be readily adjusted. The medicant-containing layer, while minimizing the likelihood of heat induced medicant damage, permits heat to be utilized to form a coating on the edible film. Hydrophilic components can be readily incorporated in larger concentrations during production of the medicant-containing layer.

SUMMARY

I have also discovered an improved composition for delivering a medicant in the oral cavity. The composition includes an applied coating and a film layer.

The film layer is made from any polymer, softener, filler, matrix, or other composition. The film has an acceptable dissolution rate in the oral cavity for a particular thickness of film. For example, if the film has a thickness of 50 microns, it may be desirable for the film to dissolve in the oral cavity within about fifteen seconds. Or it may be desirable for the film to dissolve more slowly. By way of example, and not limitation, the film can be made with pullulan, modified starch, pectin, carageenan, a maltrodextrin, or alginate.

The applied coating is a powder matrix including one or more medicants. The medicant can be contained in a powder carrier, or can itself be a powder. One advantage of the powder matrix is that it ordinarily does not require the use of a solvent. Another advantage of the powder matrix is that it ordinarily can, if desired, include in addition to the medicant a variety of different auxiliary compositions. A further advantage of the powder matrix is that it can be admixed in a fluidized bed that minimizes the generation of shear and heat. In a fluidized bed dry air or another gas is dispersed upwardly through a plurality of openings to suspend and intermix particulate. Any desired means can be used to admix powders. Another advantage of mixing or suspending powder in a fluidized bed is that the dry air suspending the powder particles tends to prevent agglomeration of the particles. The admixed powder matrix can also be stored (i.e., suspended) in the fluidized bed, prior to the application of the admixed powder matrix to the film layer. The powder matrix can be applied in any desired manner, including sifting, screening, atomization, static, mechanical agitation, etc. For example, the powder matrix can be atomized through a Nordson or similar static spray gun using compressed air. One such gun creates a fine mist spray of powder particles. The gun statically electrically charges the powder particles so they adhere to a surface of the film layer that is receiving the powder particles. Another process for applying the powder particles is to admix the particles with a liquid carrier to form a particle-liquid solution. The particle-liquid solution is sprayed on the film layer. The liquid carrier evaporates, leaving the powder particles on the film. The liquid carrier preferably does not cause the powder particles to dissolve in the liquid carrier.

One auxiliary composition that can be included in the powder matrix with the medicant is a composition that dissolves slowly over a selected period of time. Such an auxiliary dissolution control composition can be utilized to slow the release of medicant in the oral cavity. Examples of this kind of auxiliary composition are, without limitation, gel forming compositions like carrageenan, gelatin, alignates, pullulan, PVP, and other hydrophilic materials; cyclodextrin; and, inert materials like calcium and fibers. For example, the fibers can comprise carboxymethylcellulose.

Another auxiliary composition the can be included in the powder matrix with the medicant is an absorption composition that absorbs water or saliva. Such an auxiliary absorption composition can be also be used to slow the release of medicant, and/or, to form a gel. The gel can, if desired, cause the strip to become chewable, similar to a very soft jelly-bean. As used herein, an auxiliary composition is termed a gel if, when it is placed in the oral cavity or in contact with another source of bodily liquid, (1) the auxiliary composition absorbs at least four times it weight of water or of saliva or other aqueous solution in a selected period of time, or (2) the auxiliary composition swells to at least three times its thickness in a selected period of time. The selected period of time can vary but preferably is from five seconds to fifteen minutes, most preferably five seconds to five minutes. Examples of gel auxiliary compositions include, without limitation, carboxymethylcellulose, pectin, modified starches, gelatin, and carrageenan. These compositions can be used alone or in combination. One advantage of a gel is that it tends to slow the dissolution of the medicant and to maintain the medicant in the oral cavity for a longer period of time.

A further auxiliary composition that can be included in the powder matrix is a composition that, when placed in the oral cavity in contact with the mucosa therein, adheres to the mucosa. The concentration of such auxiliary adhesion compositions in the powder matrix can be adjusted to vary the length of time that the film adheres to the mucosa or to vary the adhesive forces generated between the film and mucosa. The auxiliary adhesion compositions adhere to the oral mucosa or to mucosa or tissue in other parts of the body, including the mouth, nose, eyes, vagina, and rectum. Examples of auxiliary adhesion compositions include carboxymethycellulose, polyvinyl alcohol, polyvinyl pyrrolidone (povidone), sodiumalginate, methyl cellulose, hydroxylpropyl cellulose, hydroxypropylmethyl cellulose, polyethylene glycols, carbopol, polycarbophil, carboxyvinyl copolymers, propylene glycol alginate, alginic acid, methyl methacrylate copolymers, tragacanth gum, guar gum, karaya gum, ethylene vinyl cetate, dimethylpolysiloxanes, polyoxyalkylene block copolymers, and hydroxyethylmethacrylate copolymers. All examples of composition provided herein are given without limiting the use or inclusion of other comparable or functionally equivalent compositions even though such comparable or functionally equivalent compositions are not listed.

Still another auxiliary composition that can be included in the powder matrix is a flow composition that, when subjected to a curing process, flows to form a smoother or shinier coating on the exterior of the film layer. One preferred curing process is heating the film layer with powder coating to a selected temperature above 76 degrees F. to cause the auxiliary flow composition to soften and flow. Examples of this kind of auxiliary composition are lipids (including various animal and vegetable fats) waxes, particularly low melting point waxes, and polyols, particularly low melting point polyols that can be admixed in powder form or than can included be in powder particles containing a medicant or other compositions. The medicant itself, may also have the property of flowing at an elevated temperature in excess of 76 degrees F. to form a smoother or shinier coating.

Other auxiliary compositions that can be included in the powder matrix include, without limitation, bulking agents, fillers, pigments (coloring), flavorings, and sweeteners.

Combinations of auxiliary compositions can be included in the powder matrix to achieve a desired function. For example, if it is desired to slow the dissolution of a medicant, less soluble fillers and fibers can be included in the powder matrix along with a high concentration of polymers that have a very high degree of ability to adhere to the oral mucosa lining the mouth.

The powder matrix is normally administered to the film layer to form the applied coating after the film layer has been manufactured.

The dry powder matrix will normally contain a minor amount of retained or bound water or other liquid, typically less than about ten percent by weight. The level of moisture in the powder matrix normally should not cause the powder particles to stick or adhere to one another during intermixing of powders to form the powder matrix and during application of the powder matrix to the film layer.

A medicant is an agent that cures, treats, or prevents a disease or disease symptom or condition in a body or portion of a body. By way of example, and not limitation medicants include anti-inflammatory steroids such as predonisone, predonisolone, predonisolone acetate, hydrocortisone, triamcinolone, dexamethasone, and betamethasone; anti-inflammatory anodynes such as aspirin, aminopyrin, acetoaminophen, ibufenac, ibuprofen, indomethasine, colehicine, sulpyrine, mephenamic acid, phenacetin, phenylbutazone, fulfenamic acid, and probenecid; anti-inflammatory enzymes such as (a)-chymotrysin; anti-histamine agents such as diphenhydramine-hydrocholride, and chlorophenylamine maleate; oral sterilizing agents such as chlorohexydine-hydrochloride, cetylpyridinium-chloride, hexylresorcin and nitro-furazone; antibitoc materials such as penicillin or its dervatives, cephaphalosporin derivative, erythromycine, tetracycline hydrochloride, furadiomycin, and leucomycin; chemically therapeutic agents such as sulfamethyzole and nalidixic; cardiac strengthening agents such as digatalis and digoxin; blood vein dilating agents such as nitroglycerine and papaverine-hydrochloride; local narcotic agents such as lidocain and procain-hydrochloride; cough curing agents such as codeine phosphate and bisorlvon; sore throat and mouth treatment agents such as phenol and benzocaine; periodontal disease treatment agents including peptides; digesting organ curing agents such as azulene, phenovalin, pepsin, and vitamin U; enzymes such as lysozyme-chloride or trypsin; anti-diabetic agents such as insulin; blood pressure depressing agents; tranquilizers; stypic agents; sexual hormones; agents for curing virulent carcinoma or ulcers; vitamins; and minerals. The amount of medicant incorporated with the film layer depends on the kind of drug and is usually between 0.001 to 20% by weight, but can be less or more if necessary to achieve the desired effect.

By way of example, and not limitation, the film layer can be produced using a highly water-soluble polymer comprising a natural or synthetic water-soluble polymer. The polymer preferably has good film moldability, produces a soft flexible film, and is safe for human consumption. One such polymer can be a water-soluble cellulose derivative like hydroxypropyl cellulose (HPC), methyl cellulose, hydroxypropyl alkylcellulose, carboxymethyl cellulose or the salt of carboxymethyl cellulose. Or, the polymer can comprise an acrylic acid copolymer or its sodium, potassium or ammonium salt. The acrylic acid copolymer or its salt can be combined with methacrylic acid, styrene or vinyl type of ether as a comonomer, poly vinyl alcohol, poly vinyl pyrrolidone, polyalkylene blycol, hydroxy propyl starch, alginic acid or its salt, poly-saccharide or its derivatives such as trangacanth, bum gelatin, collagen, denatured gelatin, and collagen treated with succinic acid or anhydrous phthalic acid. By way of example, the following can be included in the powder matrix as adhesives: poorly water-soluble cellulose derivatives including ethyl cellulose, cellulose acetate and butyl cellulose; shellac; higher fatty acids including steric acid and palmitic acid. The following can also, without limitation, be used to produce the film layer: pullulan, maltodextrin, pectin, alginates, carrageenan, guar gum, other gelatins, etc.

Bulking agents that can be included in the powder matrix include, by way of example and not limitation, avicel, sugar alcohols including manitol and sorbitol and xylitol and isomalt, lactic sugar, sorbitol dextrin, starch, anhydrous calcium phosphate, calcium carbonate, magnesium trisilicate, silica, and amylase.

The size of particulate in the powder matrix can vary as desired, but is preferably in the range of 10 mesh to 400 mesh or finer, preferably 40 mesh to 300 mesh.

The thickness of the film layer can vary as desired, but typically is in the range of 0.01 mm to 3.00 mm, preferably 0.03 mm to 1.00 mm.

The powder matrix can be applied to one or both sides of the film layer. The film layer includes upper outer surface on the top of the film layer and includes a lower outer surface on the bottom of the film. The upper outer surface is generally parallel to the lower outer surface. The top of the film is generally parallel to the bottom of the film. The thickness of the powder matrix layer can vary as desired, but is preferably in the range of 0.001 mm to 3.00 mm, preferably 0.01 mm to 1.00 mm.

If desired, after the powder matrix layer is applied to the film layer, an additional layer or layers can be applied over the powder matrix layer to seal the powder matrix layer, slow the dissolution of the medicant from the powder matrix layer, etc.

If desired, multiple powder matrix layers can be applied to the film layer. The film layer can comprise a laminate of two or more layers. Methods for producing the film layer and incorporating plasticizers, bulking agents, taste modifying agents, pigments, etc. in the film layer are well known in the art and not described in detail herein. Since the medicant is being applied to the film layer in a dry powder form, the likelihood of adverse interactions between the medicant and compositions comprising the film layer is lessened.

The following examples are provided by way of illustration, and not limitation, of the invention.

EXAMPLE I 3.4 g of hydropropyl cellulose and 0.4 ml of macrogol-400 (polyethylene glycol) are dissolved in 60 g of ethyl alcohol to produce a cellulose-alcohol solution. Nine milliliters of distilled water containing 90 mg of dissolved predonisolone is added to the cellulose-alcohol solution to produce a film forming composition. The film forming composition is poured into a film molding frame placed on a teflon plate. The area of teflon plate circumscribed by the frame is 9.5 square centimeters. The film forming composition is dried to form a film layer. The film layer includes an upper outer surface on top of the film layer and includes a lower outer surface on the bottom of the film layer. The lower outer surface is generally parallel to the upper outer surface. The film layer has a thickness of 40 microns. As noted, any desired prior art process and/or materials can be utilized to produce the film layer.

Benzocaine powder (as a medicant) is combined with carboxymethylcellulose powder (as an adhesive), modified food starch (as a bulking agent), carrageenan (as adhesive), sucralose (intense sweetener), talc (as flow/partitioning agent), and menthol (as a medicant) in a fluidized bed container to form a powder matrix. The resulting powder matrix includes 3.76% by weight of benzocaine powder, 2.6% by weight percent of carboxymethylcellulose powder, 85.43% by weight of modified food starch, 3.76% by weight menthol, 2% by weight carrageenan, 0.45% by weight sucralose, and 2.0% by weight magnesium trisilicate (talc). The powder matrix is drawn from the fluidized bed container and is applied to the upper exposed surface of the film layer to a substantially uniform thickness of 60 microns. The powder matrix is atomized through a Nordson or similar static spray gun using compressed air. See, for example Nordson Corporation's KINETIC™ spray systems (www.nordson.com). The gun creates a fine mist spray of powder particles. The gun statically electrically charges the powder particles so they adhere to the upper surface of the film layer. If desired the powder matrix can also be applied to the lower or bottom surface of the film layer. The powder matrix layer and film layer together comprise a medicant composition. The medicant composition can be applied to mucous membrane at various areas of the body.

EXAMPLE II

A film layer is prepared as follows. Xanthan gum (1.5% by weight), locust bean gum (1.5% by weight), carrageenan (1% by weight) and pullulan (9.5% by weight) are mixed and hydrated in hot purified water (86.5% by weight) to form a gel. The gel is stored in a refrigerator overnight at a temperature of approximately four degrees C. to form a film layer. The film layer has a thickness of 55 microns.

Coral calcium powder (as a medicant) is combined with carboxymethylcellulose powder (as an adhesive), modified food starch (as a bulking agent), carrageenan (as adhesive), sucralose (intense sweetener), talc (as flow/partitioning agent), menthol (as a medicant), and a lipid in a fluidized-bed container to produce a powder matrix. The lipid is BENEFAT™. BENEFAT is used by DANISCO to designate salatrim, which is the abbreviation for long and short chain triglyceride molecules. The resulting powder matrix includes 3.76% by weight of coral calcium powder, 2.6% by weight percent of carboxymethylcellulose powder, 73.43% by weight of modified food starch, 3.76% by weight menthol, 2% by weight carrageenan, 0.45% by weight sucralose, 2.0% by weight magnesium trisilicate, and 12% by weight of the lipid. The lipid preferably is in powder form. If the lipid initially is in liquid form, it can be plated on a particulate absorbent to produce a flowable powder. The particulate absorbent could, for example, be talc.

The powder matrix is drawn from the fluidized bed container and is applied to the upper exposed surface of the film layer to a uniform thickness of 150 microns. The powder matrix is atomized through a Nordson or similar static spray gun using compressed air. The powder matrix layer and film layer together comprise a medicant composition.

Ideally, the melting point of the lipid is close to temperature at which the film layer is dried. For example, the film layer (along with the powder matrix layer applied to the film layer) is typically dried at about 200 degrees F. The lipid preferably has a softening point or melting temperature of about 200 degrees F. so that the temperature at which the film layer is dried is the ideal softening point for the lipid. If the melting temperature of the lipid is too low in comparison to the temperature at which the film layer is dried, the lipid can melt and run off the film.

The medicant composition is cured using any desired heat treatment process. The presently preferred process comprises a first step during which the medicant composition is heated by a microwave or infrared transmitter. The time spent by the medicant composition under the transmitter varies depending on the amount of moisture to be removed, but typically is fifteen to twenty seconds. The microwave/infrared bombardment facilitates proper heating of the film layer by generating heat in the film layer. During the second step of the heat treatment process the medicant composition is heated to 200 degrees F. in a convection oven for a desired length of time to dry the medicant composition. The length of time the medicant composition is in the convection oven can vary but is typically presently about three to four minutes. During the foregoing heat treatment process, the lipid powder particles soften and flow to produce a smoother powder matrix layer on the film layer. The smoother powder matrix layer also improves the feel to an individual of the medicant composition in the mouth because the medicant composition is not as dry on the tongue.

EXAMPLE III 3.4 g of hydropropyl cellulose and 0.4 ml of macrogol-400 (polyethylene glycol) are dissolved in 60 g of ethyl alcohol to produce a cellulose-alcohol solution. Nine milliliters of distilled water containing 90 mg of dissolved predonisolone is added to the cellulose-alcohol solution to produce a film forming composition. The film forming composition is poured into a film molding frame placed on a teflon plate. The area of teflon plate circumscribed by the frame is 9.5 square centimeters. The film forming composition is dried to form a film layer. The film layer has a thickness of 30 microns.

Penicillin or another antibiotic (as a medicant) suitable for treating conjunctivitis is combined with carboxymethylcellulose powder (as an adhesive) in a fluidized bed container. The resulting powder matrix includes 5.00% by weight of the antibiotic powder, and 95% by weight of carboxymethylcellulose powder. The powder matrix is drawn from the fluidized bed container and is applied to the upper exposed surface of the film layer to a substantially uniform thickness of 5.0 microns. The powder matrix is applied with a Nordson or similar static spray gun. If desired, the powder matrix can also be applied to the lower or bottom surface of the film layer. The powder matrix layer and film layer comprise a medicant. A circular piece three-eighths inch in diameter is cut from the medicant composition. The circular piece is 35 microns thick and includes a portion of the film layer and a portion of the powder matrix layer. The circular piece is placed in an individual's eye with the powder matrix layer contacting the tear layer of the eye. The amount of adhesive in the powder matrix layer is gauged so that the powder matrix layer does not absorb moisture too rapidly from the tear layer of the individual's eye.

EXAMPLE IV

A contact lens is coated with a medicant. The medicant is released into an individual's eye when the contact lens is inserted in the eye.

EXAMPLE V

A contact lens is impregnated with a medicant. The medicant is gradually released into an individual's eye when the contact lens is inserted in the eye.

EXAMPLE VI 3.4 g of hydropropyl cellulose and 0.4 ml of macrogol-400 (polyethylene glycol) are dissolved in 60 g of ethyl alcohol to produce a cellulose-alcohol solution. Nine milliliters of distilled water containing 90 mg of dissolved predonisolone is added to the cellulose-alcohol solution to produce a film forming composition. The film forming composition is poured into a film molding frame placed on a teflon plate. The area of teflon plate circumscribed by the frame is 9.5 square centimeters. The film forming composition is dried to form a film layer. The film layer has a thickness of 50 microns.

Coral calcium powder (as a medicant) is combined with carboxymethylcellulose powder (as a fiber adhesive), modified food starch (as a soluble bulking agent), carrageenan (as adhesive), pullulan (as a polymer), calcium carbonate (as a non-soluble filler/bulking agent), sucralose (intense sweetener), talc (as flow/partitioning agent), and menthol (as a medicant) in a fluidized bed container. The resulting powder matrix includes 3.76% by weight of benzocaine powder, 5.2% by weight percent of carboxymethylcellusoe powder, 38.33% by weight of modified food starch, 5.0% by weight pullulan, 3.76% by weight menthol, 4% by weight carrageenan, 2.5% by weight talc, 0.45% by weight sucralose, 35% by weight calcium carbonate, and 2.0% by weight magnesium trisilicate.

The filler, fiber, and polymer components of the powder matrix are used to slow the dissolution of the medicant when the resulting medicant composition is placed in the oral mucosa of an individual.

The powder matrix is drawn from the fluidized bed container and is applied to the upper exposed surface of the film layer to a substantially uniform thickness of 80 microns. The powder matrix is atomized through a Nordson or similar static spray gun using compressed air. The powder matrix layer and film layer together comprise a medicant composition.

Having described my invention in such terms as to enable those of skill in the art to make and practice it, and having described the presently preferred embodiments thereof, I claim:

1. A method of manufacturing a rapidly dissolving thin film for delivering a medicant in the oral cavity, comprising the steps of:
providing a film layer, wherein the film layer is rapidly dissolving; and
applying a coating to said film layer without use of a solvent, wherein said coating comprises a powder matrix;
wherein said coating, said film layer, or both, comprises a medicant;
the method further comprising a step of heating the film layer and powder matrix to a temperature above 76 degrees F, wherein the powder matrix comprises a lipid, wax or polyol and wherein the step of heating is at a temperature at about the softening point of the lipid, wax, or polyol, such that the lipid, wax, or polyol softens and flows to form a coating on the exterior of the film layer;
the powder matrix further comprising a composition that, when placed in the oral cavity in contact with the mucosa therein, adheres to the mucosa.

2. The method of claim 1 wherein the film layer dissolves within thirty seconds of being placed in an oral cavity.

3. The method of claim 1 wherein the film layer dissolves within fifteen seconds of being placed in the oral cavity.

4. The method of claim 1 wherein said medicant is selected from the group consisting of anti-inflammatory steroids, anti-inflammatory anodynes, anti-inflammatory enzymes, antihistamine agents, oral sterilizing agents, antibiotics, chemically therapeutic agents, cardiac strengthening agents, blood vein dilating agents, local narcotic agents, cough curing agents, sore throat and mouth treatment agents periodontal disease treatment agents, digesting organ curing agents, anti-diabetic agents, other enzymes, blood pressure depressing agents, tranquilizers, styptic agents, sexual hormones, and agents for curing virulent carcinoma or ulcers.

5. The method of claim 1 further comprising the step of preparing the coating in a fluidized bed.

6. The method of claim 1 wherein the coating is applied by sifting, screening, atomization, static or mechanical agitation.

7. The method of claim 6 wherein powder particles are charged.

8. The method of claim 6 wherein the coating is applied using a static spray gun.

9. The method of claim 8 wherein the static spray gun charges the powder particles such that the powder particles adhere to the surface of the film layer.

10. The method according to claim 1 wherein the powder matrix further comprises an adhesive, a bulking agent, or a sweetener, or any combination thereof.

* * * * *